(12) United States Patent
Bianchi et al.

(10) Patent No.: US 9,834,579 B2
(45) Date of Patent: Dec. 5, 2017

(54) CRYSTALLINE FORMS OF S-ACETYL GLUTATHIONE, THEIR PREPARATIONS AND USES IN PHARMACEUTICAL AND NUTRACEUTICAL FORMULATIONS

(71) Applicant: Gnosis S.p.A., Milan (IT)

(72) Inventors: Davide Bianchi, Milan (IT); Marco Valetti, Desio (IT); Paola Bazza, Desio (IT)

(73) Assignee: Gnosis S.p.A., Desio (IT)

( * ) Notice: Subject to any disclaimer, the term of this patent is extended or adjusted under 35 U.S.C. 154(b) by 0 days.

(21) Appl. No.: 15/034,806

(22) PCT Filed: Nov. 6, 2014

(86) PCT No.: PCT/EP2014/073957
§ 371 (c)(1),
(2) Date: May 5, 2016

(87) PCT Pub. No.: WO2015/067708
PCT Pub. Date: May 14, 2015

(65) Prior Publication Data
US 2016/0272677 A1  Sep. 22, 2016

(30) Foreign Application Priority Data
Nov. 8, 2013  (IT) .............................. MI2013A1856

(51) Int. Cl.
C07K 5/02      (2006.01)
C07K 1/30      (2006.01)
A61K 38/00     (2006.01)

(52) U.S. Cl.
CPC ............ C07K 5/0215 (2013.01); C07K 1/306 (2013.01); *A61K 38/00* (2013.01)

(58) Field of Classification Search
CPC ............................. C07K 5/0215; A61K 38/063
See application file for complete search history.

(56) References Cited

U.S. PATENT DOCUMENTS

| 2,760,956 | A | * | 8/1956 | Brick ................. C07K 5/02 530/332 |
| 5,382,679 | A | * | 1/1995 | Galzigna .......... C07K 5/0215 549/78 |
| 2009/0136993 | A1 | | 5/2009 | Bridge |

FOREIGN PATENT DOCUMENTS

WO    9200320 A1    1/1992

OTHER PUBLICATIONS

Caira, M. R., Crystalline Polymorphism of Organic Compounds. Topics in Current Chemistry. Jan. 1, 1998. vol. 198 pp. 163-208.
Fraternale, A, Inhibition of murine AIDS by pro-glutathione (GSH) molecules. Antiviral Res. Feb. 2008;77(2):120-7. Abstract Only.
Locigno, R, S-acetyl-glutathione selectively induces apoptosis in human lymphoma cells through a GSH-independent mechanism. Int J Oncol. Jan. 2002;20(1):69-75. Abstract Only.
Okun, JG, S-Acetylglutathione normalizes intracellular glutathione content in cultured fibroblasts from patients with glutathione synthetase deficiency. J Inherit Metab Dis. 2004;27(6):783-6. Abstract Only.
Vogel, Ju, Effects of S-acetylglutathione in cell and animal model of herpes simplex virus type 1 infection. Med Microbiol Immunol. Jan. 2005;194(1-2):55-9. Abstract Only.
Witschi, A., et al., The systemic availability of oral glutathione. Eur J Clin Pharmacol. 1992;43(6):667-9. Abstract Only.

\* cited by examiner

*Primary Examiner* — Christina Bradley
(74) *Attorney, Agent, or Firm* — Amin Talati Upadhye LLP; George M. Carrera, Jr.; Yichen Cao

(57) ABSTRACT

Disclosed are two novel crystalline forms of S-acetyl glutathione (SAG) called Form A and Form B, obtained by crystallization of SAG from mixtures of water-acetone, water-ethanol or water acetone under controlled conditions. Forms A and B can be advantageously used as ingredients of pharmaceutical or nutraceutical formulations.

10 Claims, 14 Drawing Sheets

GSH

SAG

CRYSTALLINE FORMS OF S-ACETYL GLUTATHIONE, THEIR PREPARATIONS AND USES IN PHARMACEUTICAL AND NUTRACEUTICAL FORMULATIONS

This application is a U.S. National Stage application under 35 U.S.C. §371 of International Application No. PCT/EP2014/073957, filed on Nov. 6, 2014 that claims priority to an Italian application, MI2013A001856, filed on Nov. 8, 2013, each of which are hereby incorporated by reference herein.

FIELD OF INVENTION

The present invention relates to novel crystalline forms of S-acetyl glutathione (SAG) which are useful in the preparation of pharmaceutical or nutraceutical compositions.

BACKGROUND TO THE INVNETION

Glutathione (GSH) is a compound which, in its reduced form, constitutes an excellent antioxidant and therefore a defence against the damage caused by free radicals to higher organisms. S-acetyl-glutathione (SAG) (see FIG. 1) is a synthetic derivative thereof which protects GSH against oxidation, and simultaneously releases it easily by hydrolysis.

GSH or γ-L-glutamyl-L-cysteinylglycine is a tripeptide consisting of glutamic acid, cysteine and glycine, characterised by an atypical peptide bond, namely the bond that binds the nitrogen of cysteine to the carboxyl in γ glutamic acid. It is the main thiol compound with the lowest molecular weight present in both animal and plant cells (about 95% of the total). Its function is to maintain in the reduced state the —SH groups of many enzymes and proteins whose oxidation (with the formation of S—S intra- and intermolecular disulphide bridges) leads, in most cases, to inactivation or loss of the biological function of the enzyme or protein.

GSH is considered to be one of the most important intracellular antioxidants produced naturally by the human body. However, chronic oxidative stress reduces the cell levels of GSH, and it is often appropriate to replenish its levels with the aid of diet supplements.

It is commonly believed that the GSH intake obtained from the diet or with the use of diet supplements is easily used by the issues, but in reality it is not absorbed "as is", but hydrolysed into its three constituent amino acids by a gamma-glutamyl transpeptidase present in the intestine. After being absorbed and introduced into the bloodstream, said amino acids are distributed to the various tissues wherein they implement the pool of amino acids with which the body cells synthesise endogenous GSH. It is therefore necessary to use a high oral dose in order to guarantee significant absorption. When Witschi et al. evaluated the increase in the blood levels of glutathione, cysteine and glutamate after oral administration of GSH to seven healthy volunteers, no significant increases were observed at doses of up to 3 g per dose (Witschi A et al., J. Clin. Pharmacol. 43 (6), 667-1992).

Sublingual administration, which guarantees better bioavailability, can be used as an alternative to oral administration of GSH.

Finally, in the pharmaceutical field, prophylaxis based on GSH is used in some cases by parenteral, intramuscular or slow intravenous administration, for example as prophylaxis for neuropathy resulting from chemotherapy with cisplatin or analogues.

The use of SAG as a precursor is a good alternative to replenish the reduced GSH levels in the body. In fact, acetylation of the sulphur atom prevents the decomposition of GSH and facilitates its absorption through the intestinal wall, thus enabling the molecule to pass extensively into the cells.

The SAG thus assimilated by the tissues is hydrolysed by cytoplasmic thioesterase and, by hydrolysis of the acetyl group, produces reduced GSH which is available for all the biological functions wherein it is required.

The addition of SAG to cultures of fibroblasts originating from individuals suffering from a genetic glutathione synthetase deficiency has proved able to replenish the intracellular level of GSH effectively (Okun J G et al., J. Inherit. Metab. Dis. 27(6), 783-2004). SAG is also more stable in the plasma and has proved more effective than GSH in replenishing the cell levels of GSH impoverished by viral infections (Vogel J U et al., Med. Microbiol. Immunol. 194, 55-2005) (Fraternale A et al., Antiviral Res. 77, 120-2008). Finally, SAG exhibits an interesting non-GSH-dependent activity that induces apoptosis in some human tumour cell lines in vitro. (Locigno R et al., Int. J. Oncol. 20, 69-2002).

Identification and characterisation of the polymorphic forms, and of the experimental conditions for obtaining them, are very important parameters for a compound designed for nutraceutical and/or pharmaceutical use.

The synthesis of SAG has already been claimed in a Japanese patent (see Chemical Abstract 97-7222755s) and in WO92/00320. However, the authors only disclose a general method for obtaining it, without investigating the existence of polymorphic forms in any way.

As stated above, a number of difficulties are involved in the absorption of GSH, which are partly solved by the use of the SAG derivative. However, the absorption of said compound may be adversely affected by the existence of polymorphic forms thereof having different physicochemical characteristics that influence its dissolution rate, solubility and therefore bioavailability, not to mention the different behaviour of the powders during the preparation of the various formulations.

No experimental condition or preliminary indication for crystallisation and drying that suggests the existence of polymorphic forms of SAG has ever been disclosed in any patent or patent application.

DESCRIPTION OF THE INVENTION

We have now surprisingly found that SAG exists not only in the amorphous form, but also in at least two polymorphic forms characterised by different physicochemical properties, which are useful as ingredients of pharmaceutical or nutraceutical compositions.

The experimental evidence for the existence of said two polymorphic forms, described in the present invention as form A and form B, is supplied by the analyses described below, conducted both in solution and in the solid state.

The samples of the two crystalline forms subjected to 1H-NMR analysis (FIGS. 2, 2A, 3 and 3A) produced a spectrum highly consistent with the chemical formula of the stated compound, indicating that there is no spectral difference between them in solution.

Conversely, the analyses performed directly on the substance in the solid state clearly demonstrate the presence of polymorphic forms.

Figure 4:
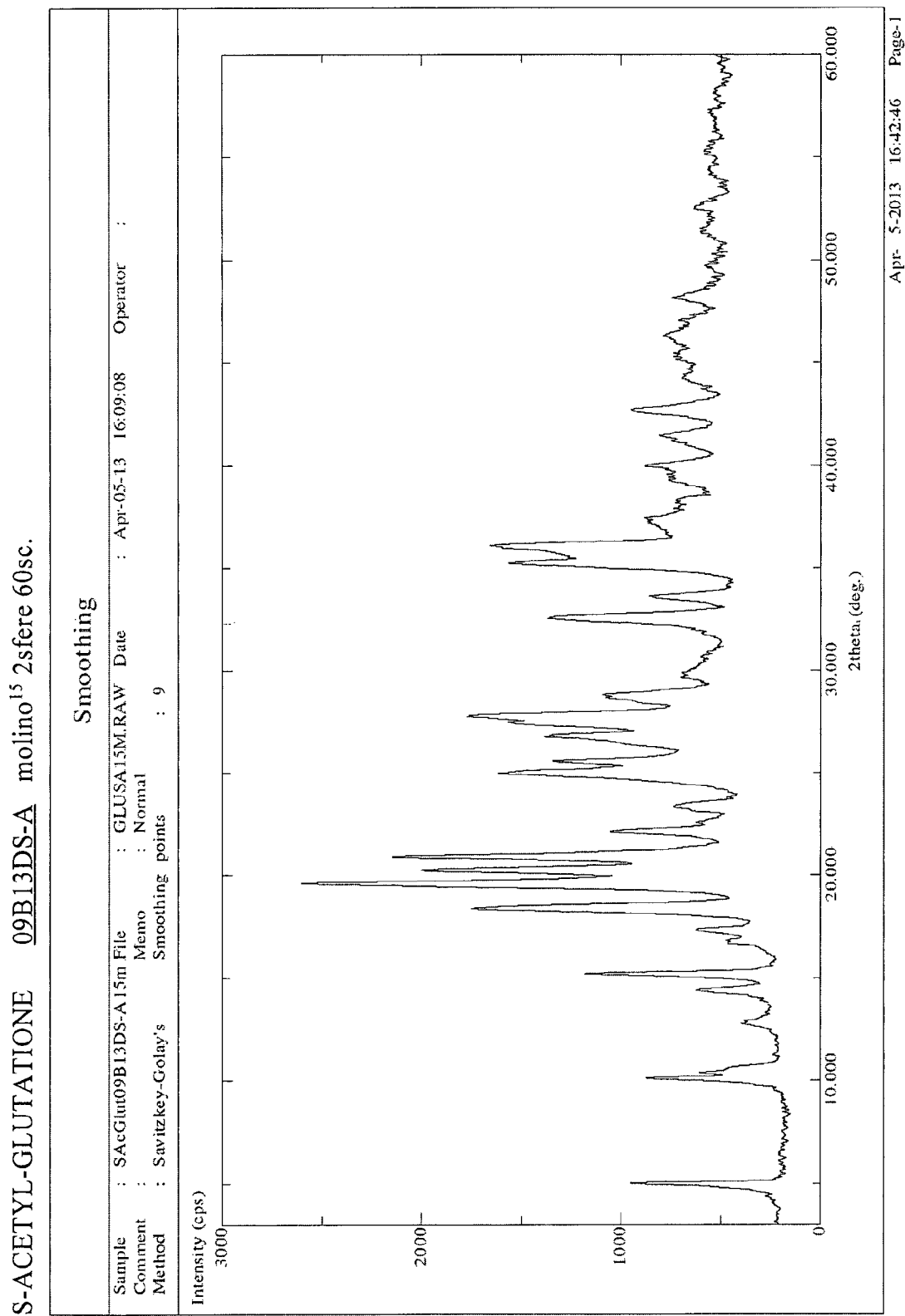
FIG. 4: XRD diffractogram of SAG form A
Figure 5:
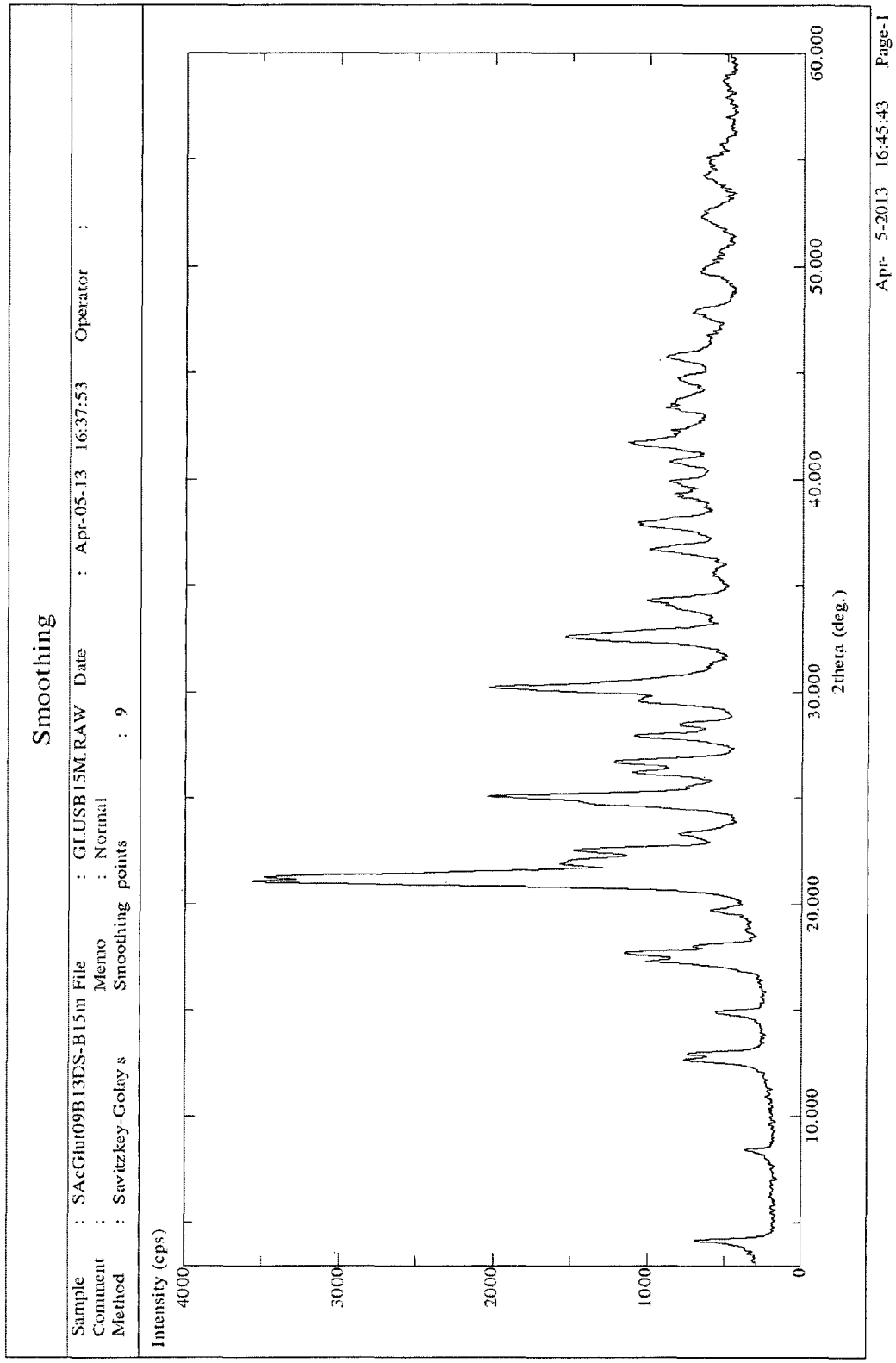
FIG. 5: XRD diffractogram of SAG form B

XRD: the analyses conducted with the X-ray diffractometer indicated significant differences in the crystallographic properties of the two samples (FIGS. 4 and 5). The number and intensity of no less than 20 diffraction peaks clearly indicate that they possess two different cell types, and therefore that there are two distinct crystalline forms of the same chemical compound.

Tables 1 and 2 show the best-resolved diffraction peaks, relating to polymorphic forms A and B respectively. The values shown in bold type correspond to the peaks characterising the two forms.

TABLE 1

| 2 theta [°] | d-value | I/I$_0$ |
|---|---|---|
| 5.2 | 17.1113 | 63 |
| 10.3 | 8.6143 | 55 |
| 15.4 | 5.7636 | 76 |
| 18.6 | 4.7765 | 100 |
| 19.7 | 4.4981 | 81 |
| 20.4 | 4.3496 | 71 |
| 21.1 | 4.2148 | 87 |
| 25.1 | 3.5420 | 70 |
| 25.7 | 3.4607 | 76 |
| 27.0 | 3.3043 | 57 |
| 27.6 | 3.2337 | 76 |
| 27.9 | 3.1928 | 98 |
| 32.7 | 2.7346 | 77 |
| 35.3 | 2.5376 | 66 |
| 36.3 | 2.4753 | 84 |

TABLE 2

| 2 theta [°] | d-value | I/Io |
|---|---|---|
| 4.2 | 21.2221 | 20 |
| 12.7 | 6.9861 | 22 |
| 13.0 | 6.8251 | 21 |
| 14.9 | 5.9405 | 16 |
| 17.3 | 5.1214 | 29 |
| 17.7 | 5.0122 | 33 |
| 21.0 | 4.2227 | 100 |
| 21.3 | 4.1717 | 98 |
| 21.9 | 4.0513 | 45 |
| 22.5 | 3.9413 | 43 |
| 24.7 | 3.5956 | 40 |
| 25.1 | 3.5476 | 59 |

TABLE 2-continued

| 2 theta [°] | d-value | I/Io |
|---|---|---|
| 30.2 | 2.9568 | 58 |
| 32.6 | 2.7477 | 44 |

IR: here again, the spectra recorded by FTIR on the substances in the solid state (FIGS. 6 and 7) exhibited different spectral bands, clearly indicating the presence of two different crystalline forms. Form A presents (inter alia) a characteristic NH stretching band at 3344 cm$^{-1}$ and characteristic carbonyl stretching bands at 1726, 1687 and 1663 cm$^{-1}$. Form B presents (inter alia) characteristic NH stretching bands at 3370 and 3355 cm$^{-1}$ and characteristic carbonyl stretching bands at 1701, 1677 and 1648 cm$^{-1}$.

Although the 1H-NMR spectra excluded the presence of solvents, the samples were also subjected to thermal analyses, namely TGA and DSC.

Figure 8:
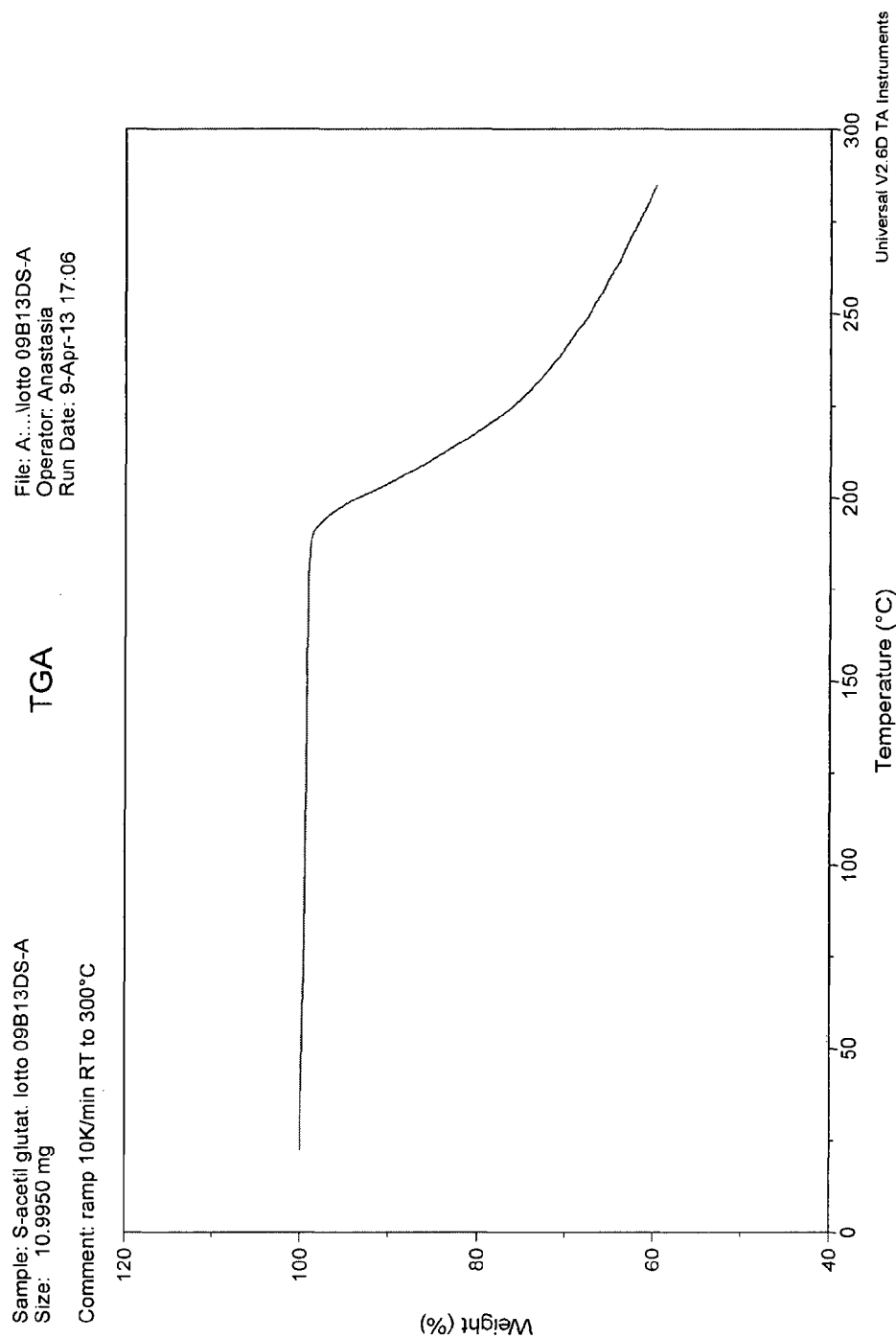
FIG. 8: thermogravimetric analysis (TGA) of SAG form A
Figure 9:
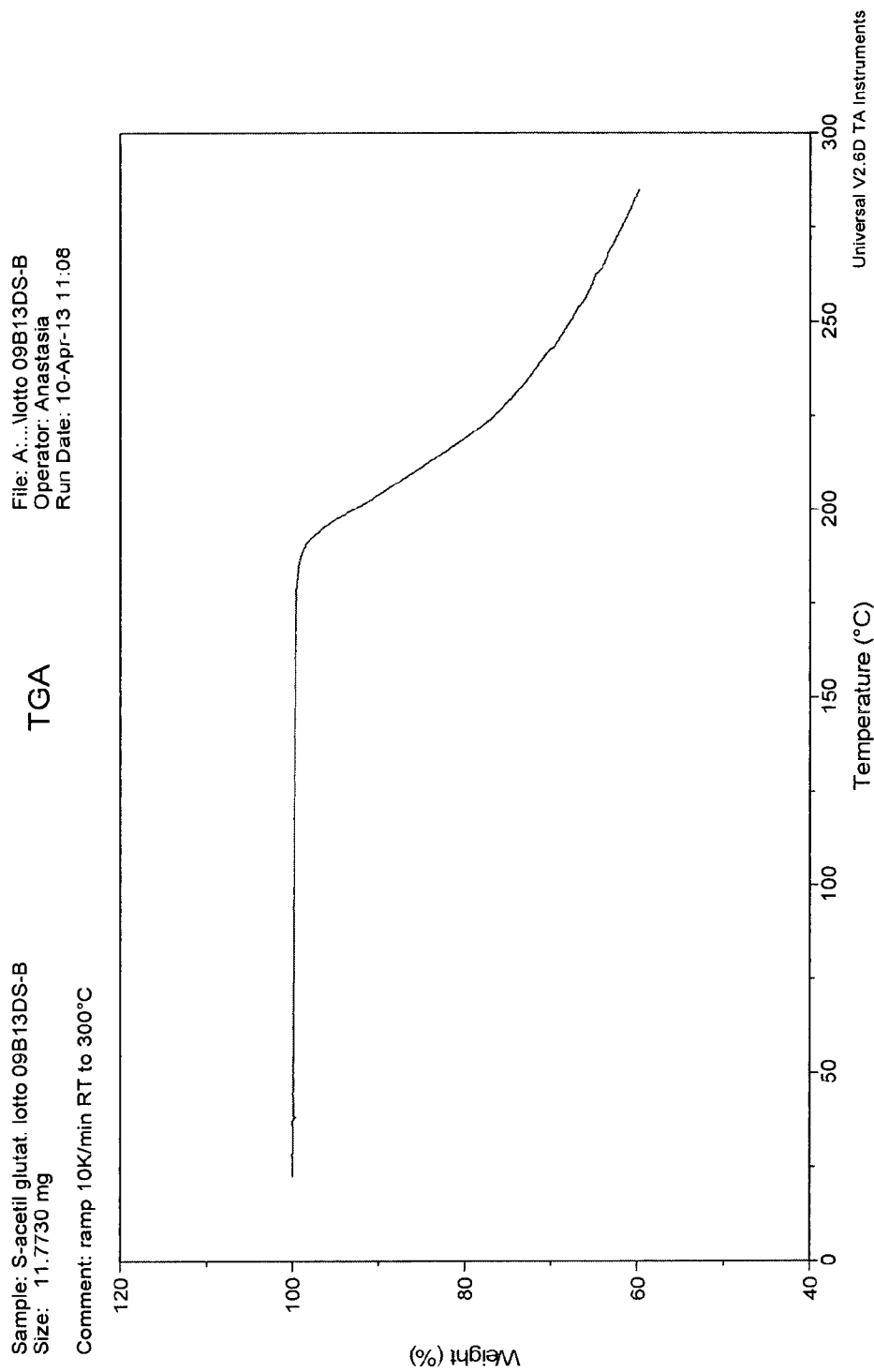
FIG. 9: thermogravimetric analysis (TGA) of SAG form B

TGA: thermogravimetric analyses, conducted on two samples, categorically exclude the presence of "solvates" and indicate a marked weight loss, due to decomposition, at a temperature much higher than 150° C. (FIGS. 8 and 9).

Figure 10:
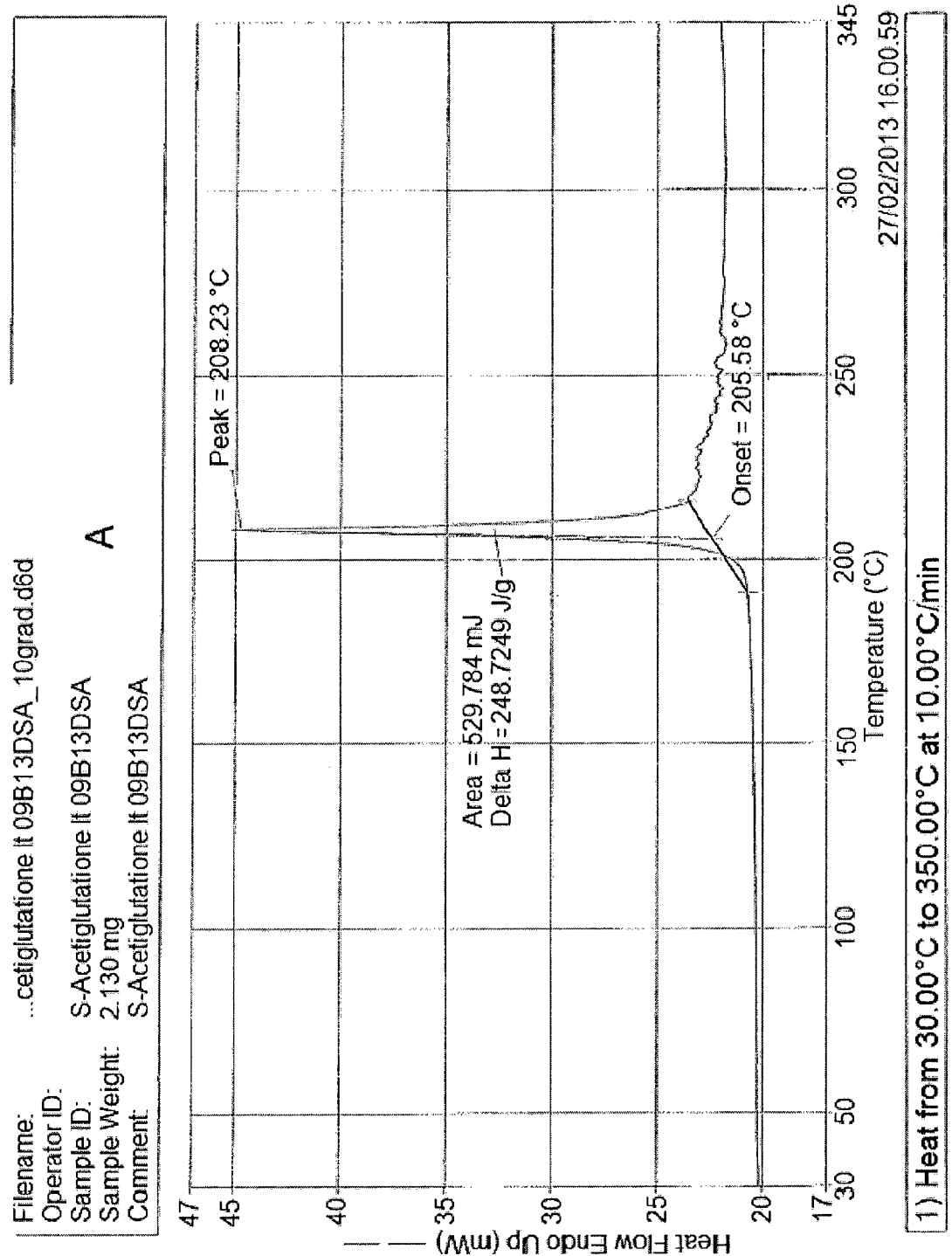
FIG. 10: DSC thermogram of SAG form A
Figure 11:
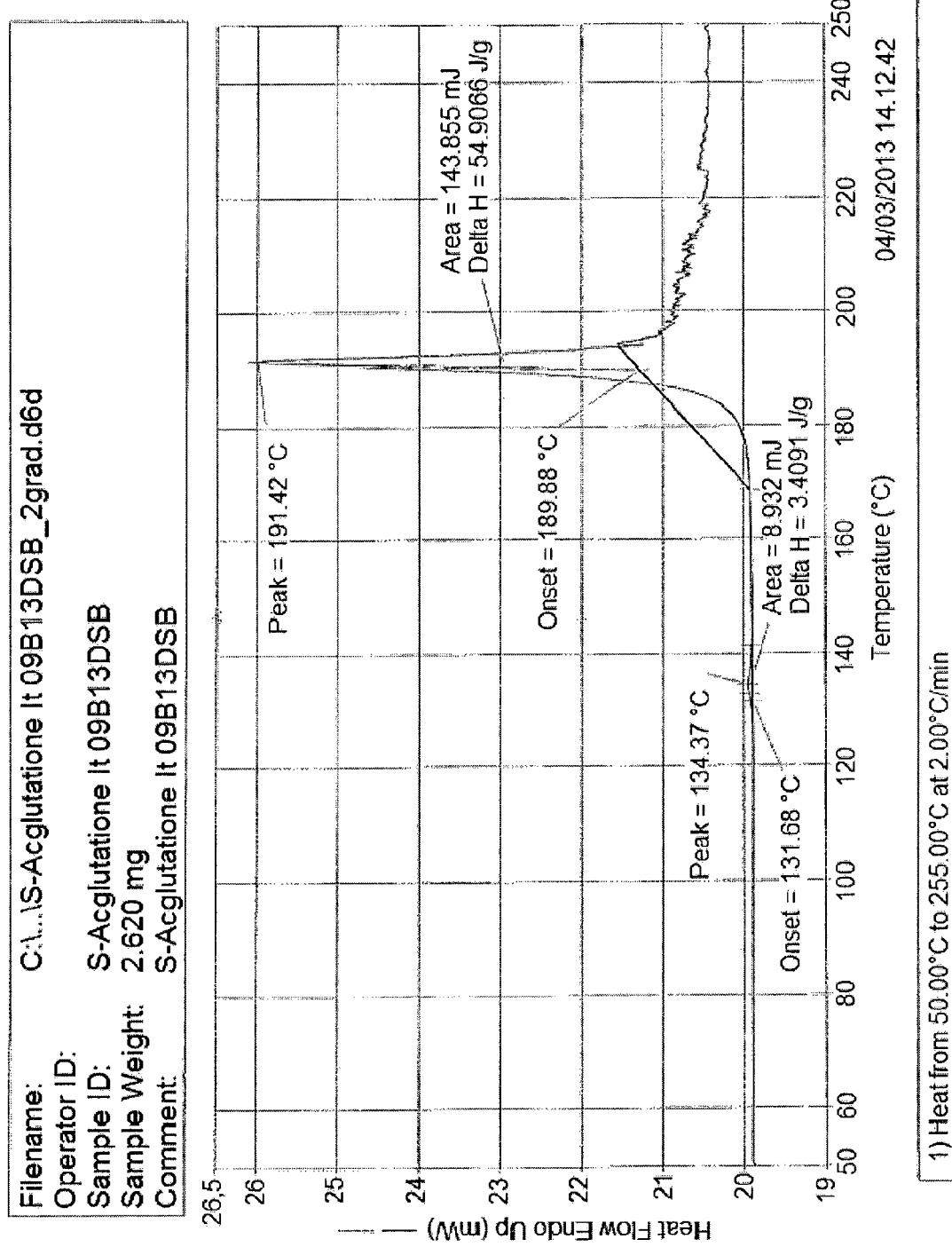
FIG. 11: DSC thermogram of SAG form B

DSC: The thermograms confirm decomposition at around 200° C. in both polymorphs, and although the endothermic peak, at 208.2° C. for form A and 191.4° C. for form B, presents a fairly clear start which could misleadingly indicate a fusion, it relates to decomposition with weight loss (FIGS. 10 and 11).

Figure 12:
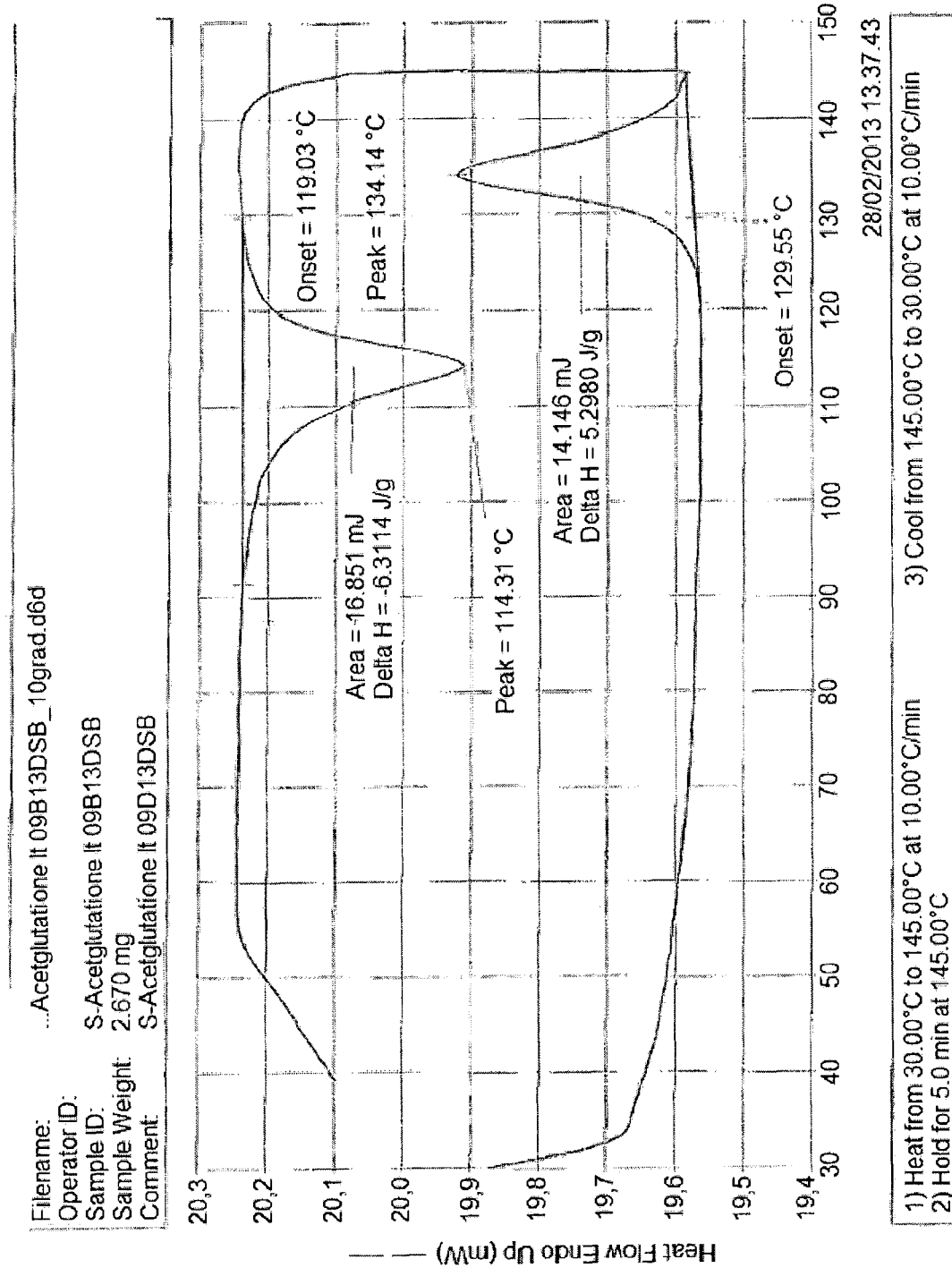
FIG. 12: DSC cooling thermogram of SAG form B

However, the two thermograms differ in terms of the presence, in polymorph B, of a weak endothermic event at about 135° C. Said event, which is perfectly reversible, can be seen in the cooling thermogram of the compound, as an analogous exothermic event at a slightly lower temperature (FIG. 12).

On the basis of these data, it can therefore be concluded that SAG exists in at least two different polymorphic forms, A and B, characterised by different physicochemical properties.

One object of the present invention is therefore a crystalline form of SAG called form A, characterised by an X-ray powder diffraction spectrum, obtained with α$_1$ (λ=1.54060 Å) and α$_2$ (λ=1.54439 Å) copper radiation, as shown in FIG. 4, and having characteristic peaks, expressed in degrees 2-theta [°], at 5.2, 10.3, 15.4, 18.6, 19.7, 35.3, 36.3±0.2.

In the XRD diffractogram, an additional group of characterising diffraction peaks, expressed in degrees 2-theta [°], is represented by those at 20.4, 21.1, 25.1, 25.7, 27.0, 27.6, 27.9, 32.7±0.2.

Figure 6:
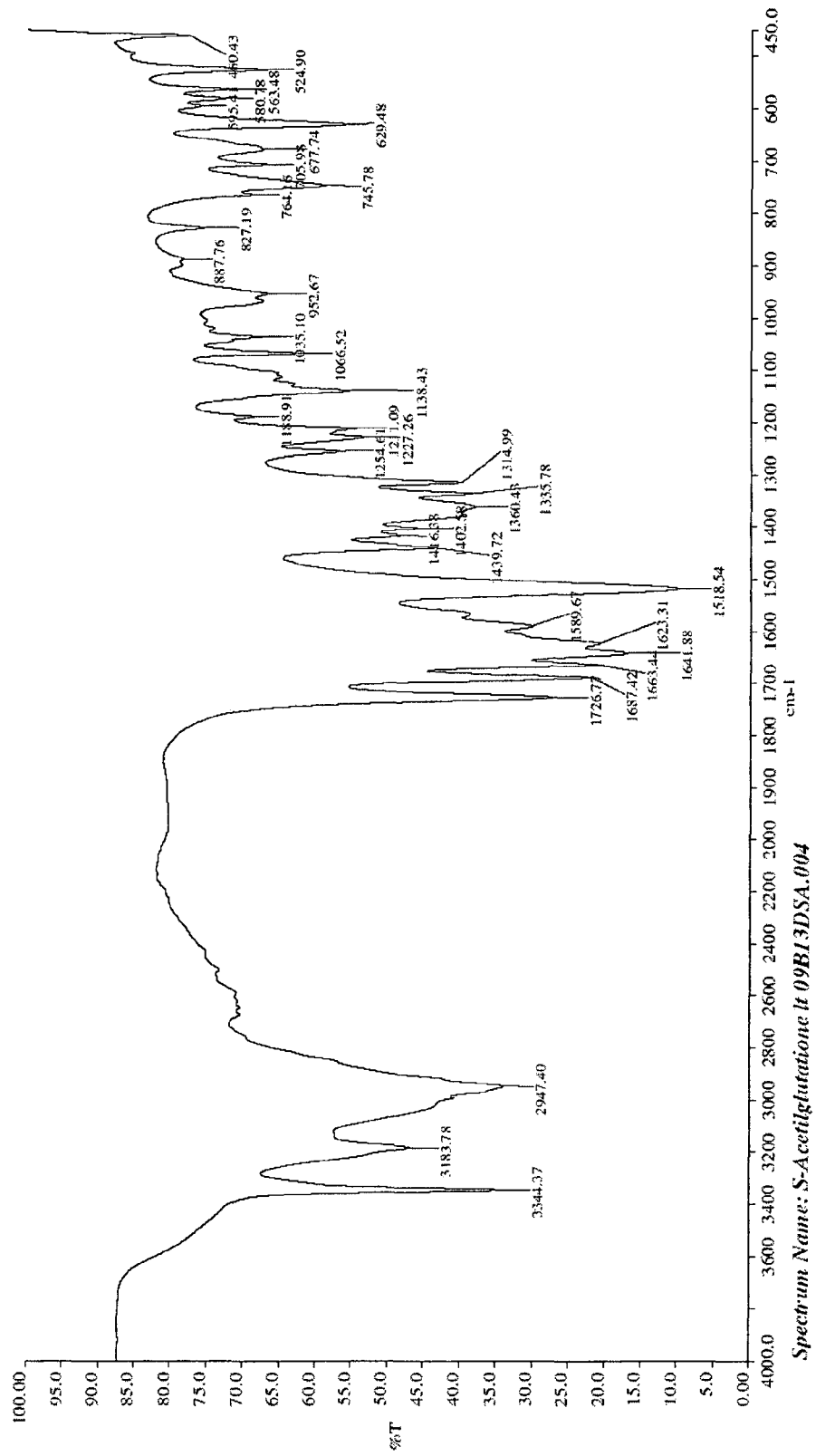
FIG. 6: FTIR spectrum of SAG form A

Crystalline form A is characterised by an IR spectrum, obtained with a potassium bromide matrix, as shown in FIG. 6, having characteristic absorption bands at 3344, 1726, 1687 and 1663 cm$^{-1}$ (inter alia).

Crystalline form A is also characterised by a DSC pattern, obtained with a heating rate of 10.00° C./min, having an endothermic peak between 190° C. and 210° C., connected to the decomposition of the compound, followed by other disorderly endothermic events, as shown in FIG. 10.

Another object of the present invention is a crystalline form of SAG called form B, characterised by an X-ray powder diffraction spectrum, obtained with α$_1$ (λ=1.54060 Å) and α$_2$ (λ=1.54439 Å) copper radiation, as shown in FIG. 5 and having characteristic peaks, expressed in degrees 2-theta [°], at 4.2, 12.7, 13.0, 17.3, 17.7, 30.2±0.2. In the XRD diffractogram, an additional group of characterising diffraction peaks, expressed in degrees 2-theta [°], is represented by those at 14.9, 21.0, 21.3, 21.9, 22.5, 24.7, 25.1, 32.6±0.2.

Figure 7:
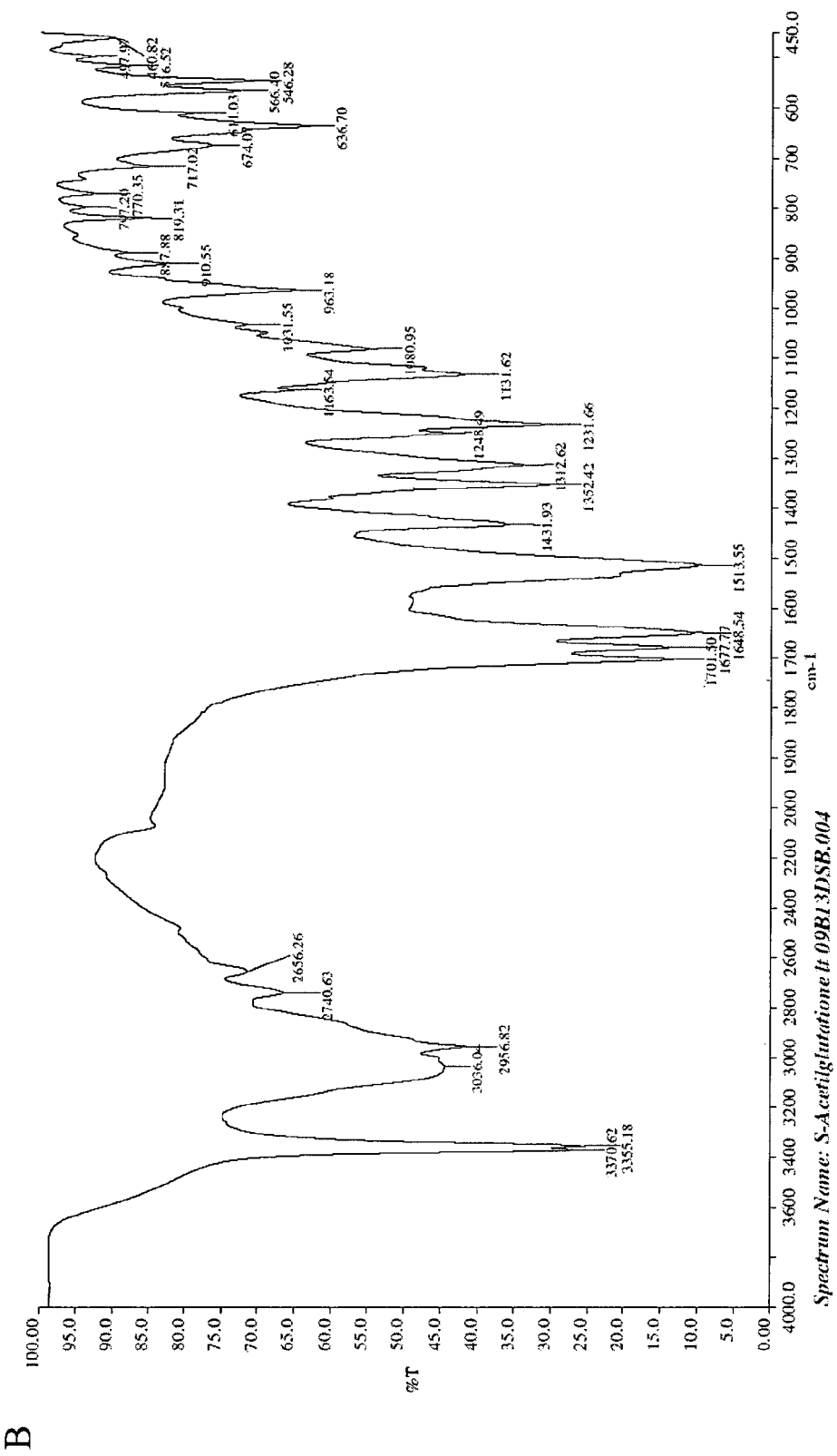
FIG. 7: FTIR spectrum of SAG form B

Crystalline form B is characterised by an IR spectrum, obtained with a potassium bromide matrix, as shown in FIG. 7, having characteristic absorption bands at 3370, 3355, 1701, 1677 and 1648 cm$^{-1}$ (inter alia).

Crystalline form B is also characterised by a DSC pattern, obtained with a heating rate of 10.00° C./min, having an endothermic decomposition peak between 180° C. and 200° C., connected to the decomposition of the compound, followed by other disorderly endothermic events, and a characteristic endothermic peak at about 135° C., as shown in FIG. 11.

A further object of the present invention is a method for the production of crystalline forms A and B of SAG with high yields and chemical purity.

Crystalline forms A and B are obtainable by crystallising SAG with mixtures of solvents such as water-acetone, water-ethanol and water-methanol, preferably water-acetone.

The most surprising finding, which in particular is not easily deducible even by the skilled person, is that all the mixtures of said solvents are able to provide both polymorph A and polymorph B, and that the discriminating factor is the conditions wherein crystallisation is triggered.

In fact, the addition of the precipitation solvent (non-solvent) before crystallisation is triggered by water gives rise to polymorphic form B, whereas if crystallisation is triggered by water alone and the non-solvent is only added to increase the yields (complete the precipitation), polymorphic form A is obtained. This behaviour is confirmed by the precipitation of both polymorphs A and B if the triggering of the crystallisation from water is allowed and the solvent (non-solvent) is added before precipitation of the product is complete.

Crystalline form A of SAG can be prepared by a process comprising the following steps:
a) dissolution of SAG in water at a temperature ranging between 75° C. and 80° C.;
b) immediate cooling of the solution obtained in step a) to a temperature of below 55° C., preferably to a temperature ranging between 45° C. and 55° C., followed by further cooling until incipient crystallisation;
c) cooling to 20-25° C. of the mass obtained in step b) in the presence of minimal stirring (60-120 rpm), followed by continued stirring of the mass at 20-25° C. for between 2 and 12 hours;
d) slow addition to the suspension obtained in c) of a solvent selected from the group containing acetone, ethanol and methanol, preferably acetone, followed by cooling of the resulting suspension to a temperature ranging between 3° C. and 7° C.;
e) isolation of the solid that separates in step d), to give crystalline form A of SAG.

Crystalline form B of SAG can be prepared by a process comprising the following steps:
a) dissolution of SAG in water at a temperature ranging between 75° C. and 80° C.;
b) immediate cooling of the solution obtained in step a) to a temperature of 55° C., followed by addition of a solvent selected from the group containing acetone, ethanol and methanol, preferably acetone;
c) spontaneous cooling to 20-25° C. of the mass obtained in step b) in the presence of minimal stirring (60-120 rpm), followed by continued stirring of the mass at 20-25° C. for between 2 and 12 hours;
d) cooling of the suspension obtained in step c) to a temperature ranging between 3° C. and 7° C.;
e) isolation of the solid that separates in step d), to give crystalline form B of SAG.

Conversely, the amorphous form can be obtained by spray-drying of an aqueous solution of the product.

The two polymorphic forms A and B and the amorphous form present different physicochemical properties, in particular as regards the quality of the product, its stability, its dissolution rate in water, and the density and flowability of the powders. Quality, assay value and stability of the various forms—Crystalline forms A and B differ due to the presence of different quantities of oxidised GSH (GSSG), because the crystallisation of polymorph A gives rise to an increase in GSSG (about 1% more). This GSSG does not only derive from oxidation of the residual GSH present in the reaction environment, but also of that deriving from hydrolysis of SAG during crystallisation, albeit in minimal quantities. The percentage of GSSG is much higher in the amorphous form due to the drying conditions, which increase hydrolysis and the corresponding oxidation. This does not affect the quality of the product, because GSSG, like SAG, is able to replenish GSH after absorption.

When samples of polymorphs A and B were subjected to heat and mechanical stresses, the possibility of conversion of one polymorph to the other under the conditions used was not found.

The stability of the various solid forms was tested as described in the European Pharmacopoeia (EP), by conducting accelerated stability tests at 50° C. for 6 months. The results are set out in Table 3 as internal standardisation (% areas of ingredients) and as SAG assay value.

TABLE 3

| Months | Type of solid | Unknown impurities (total) | Unknown impurities (single) | GSH | GSSG | SAG | SAG - assay value |
|---|---|---|---|---|---|---|---|
| 0 | Amorphous | 1.4% | 0.4% | 1.0% | 2.5% | 95.1% | 96.5% |
| 1.5 | Amorphous | 1.9% | 0.9% | 1.6% | 2.5% | 94.6% | 94.9% |
| 3 | Amorphous | 2.3% | 1.2% | 2.4% | 2.8% | 91.3% | 92.4% |
| 4.5 | Amorphous | 2.7% | 1.3% | 2.8% | 2.9% | 90.4% | 91.5% |
| 6 | Amorphous | 3.5% | 1.5% | 2.5% | 3.9% | 88.6% | 89.9% |
| 0 | Form A | 1.0% | 0.4% | 0.1% | 2.2% | 96.3% | 98.6% |
| 1.5 | Form A | 1.7% | 0.5% | 0.1% | 2.2% | 95.5% | 98.3% |
| 3 | Form A | 1.9% | 0.5% | 0.2% | 2.3% | 95.1% | 97.8% |
| 4.5 | Form A | 2.0% | 0.7% | 0.2% | 2.4% | 94.7% | 97.6% |
| 6 | Form A | 2.0% | 0.9% | 0.3% | 2.4% | 94.4% | 97.4% |
| 0 | Form B | 0.8% | 0.2% | 0.2% | 1.1% | 97.7% | 99.3% |
| 1.5 | Form B | 0.9% | 0.5% | 0.3% | 1.2% | 97.1% | 99.1% |
| 3 | Form B | 1.1% | 0.7% | 0.7% | 0.8% | 96.7% | 98.7% |

TABLE 3-continued

| Months | Type of solid | Unknown impurities (total) | Unknown impurities (single) | GSH | GSSG | SAG | SAG - assay value |
|---|---|---|---|---|---|---|---|
| 4.5 | Form B | 1.3% | 0.7% | 0.9% | 1.1% | 96.0% | 98.3% |
| 6 | Form B | 2.0% | 0.8% | 1.0% | 0.9% | 95.7% | 98.1% |

As will be seen from the data in Table 3, the amorphous form is much less stable than the crystalline forms, and of the latter, polymorphic form B is characterised by a higher purity and assay value.

Dissolution Rate—

Of the two crystalline forms, form B has the most rapid dissolution rate, and is therefore the most suitable for oral formulations, whose dissolution rate influences the absorption rate. Only the amorphous form dissolves more rapidly, but the quality and stability of the product are unsuitable for its use.

Powder Density—

As regards this aspect, study of the two crystalline forms demonstrates that polymorphic form B has a higher density (0.4 g/mL) than form A (0.2-0.25 g/mL) This parameter influences the flowability and compressibility of the powder, and therefore its use for the preparation of solid formulations, especially tablets. The powders of polymorphic form A therefore present better flowability.

Crystalline forms A and B of SAG can be formulated in pharmaceutical or nutraceutical compositions suitable for oral or parenteral administration, using conventional techniques and excipients.

A further object of the present invention is therefore pharmaceutical or nutraceutical compositions containing crystalline forms A and B of SAG.

A further object is the use of crystalline forms A and B of SAG for the preparation of medicaments or diet supplements.

A further object is the use of crystalline forms A and B of SAG for the preparation of vials containing powdered SAG for injectable parenteral administration.

The following examples further illustrate the invention.

EXAMPLES

The XRD spectra were obtained with a RIGAKU-MINIFLEX diffractometer. The radiations used were $\alpha_1$ and $\alpha_2$ ($\lambda$=1.54060 Å and $\lambda$=1.54439 Å, respectively) copper radiation.

The FTIR spectra were obtained with a Perkin-Elmer FTIR Spectrum-one instrument. The samples were analysed as KBr tablets without vacuum, with a 1:100 dilution.

The TGA patterns were obtained with a Universal V2.6D TA instrument. The temperature range explored was 0° C.→300° C., with a scanning rate of 10° C./min.

The DSC thermograms were obtained with a Perkin Elmer DSC6 instrument. The temperature range explored was 30° C.→350° C., with a scanning rate of 10° C./min. In the case of FIG. 12, the DSC thermogram was obtained by heating from 30° C. to 145° C. at the rate of 10° C./min, the sample then being maintained for 5 min at 145° C. and finally cooled from 145° C. to 30° C. at the rate of 10° C./min.

The 1H-NMR spectra were obtained with a Varian Gemini 200 instrument operating at 200 MHz, using $D_2O$ as solvent.

Example 1

Preparation of SAG in Crystalline form A 5 g of crude SAG is placed under stirring and heated to 75° C. in 40 mL of demineralised water. The reaction mass is heated to 75° C.-80° C. After dissolution, the solution is immediately cooled to a temperature of under 55° C., preferably between 45 and 55° C. Cooling continues until crystallisation begins. Stirring is minimised and the solution is cooled to 20-25° C., at which temperature it is left under stirring for 2-12 h until precipitation is complete. Subsequently, again with minimal stirring, 40 mL of acetone is added in about 30-50 min. The addition is slow to prevent the formation of even a few crystals of polymorph B. The resulting suspension is then brought to 5° C.±2° C. and maintained under slow stirring (60-120 rpm) for about 1 h. At the end of that time the reaction mass is filtered to obtain a white solid, which is washed with anhydrous acetone (2×10 mL) 8.4 g of wet solid is thus obtained, which is left to dry at 50° C., 5 mbar of residual vacuum for 14-18 h. 4.3 g (86%) of white crystalline solid corresponding to crystalline form A is obtained after drying.

The analytical profile of the product thus obtained is:

Assay value: 98.6% (as is)

Impurities: Total: 1.0%; Single known impurities: GSH (0.1%), GSSG (2.2%);

Water 1.4%

Residual acetone: <500 ppm

Residual acetic acid: 0.4%

Apparent density: 0.15-0.25 g/mL

Figure 1:
FIG. 1: glutathione (GSH) and S-acetyl glutathione (SAG) structures
Figure 1:
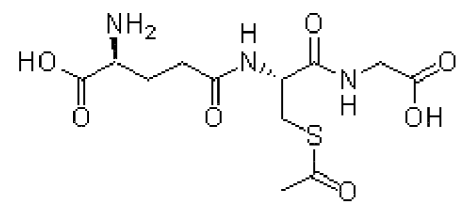
Figure 2:
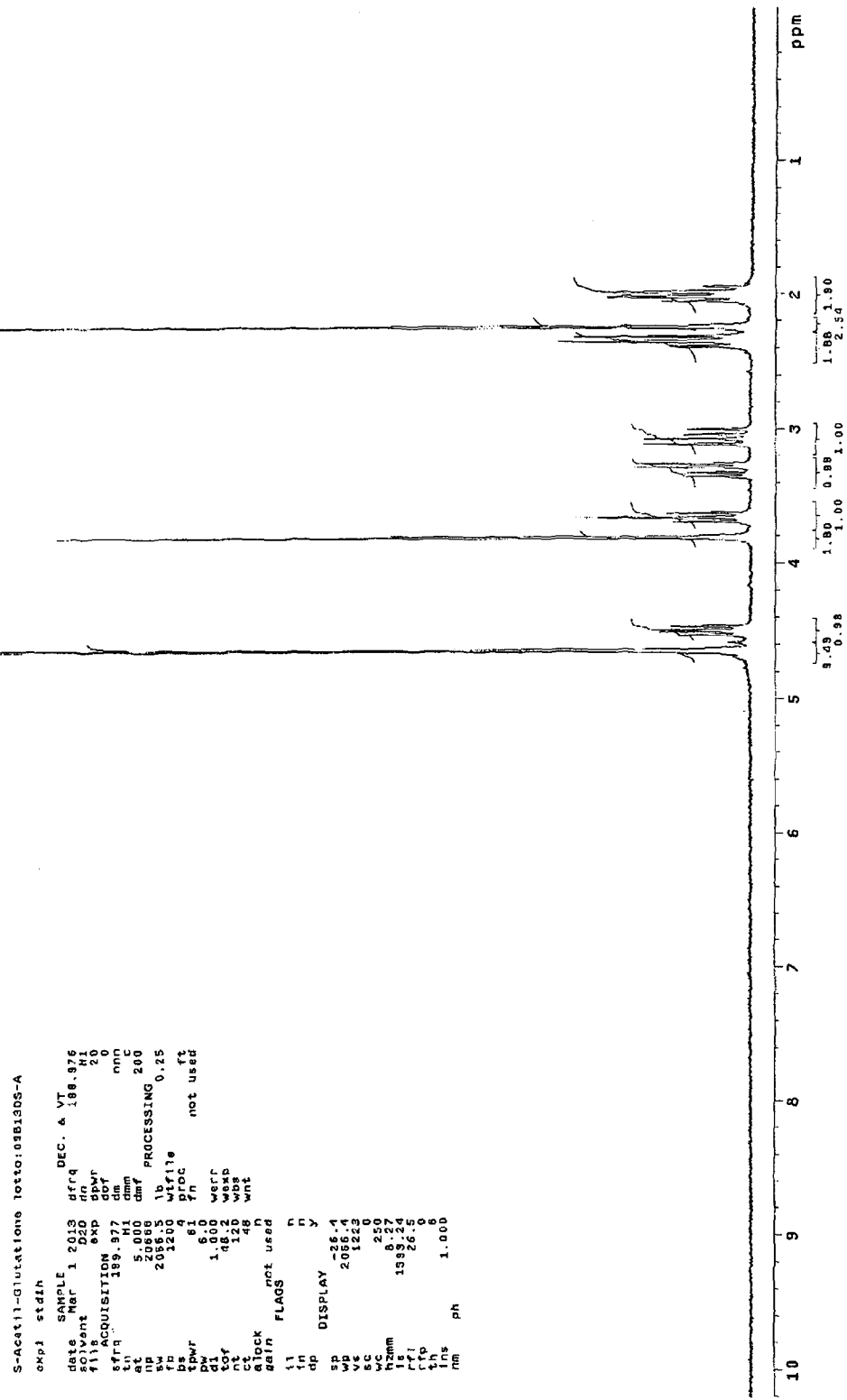
FIG. 2: 1H-NMR spectrum of SAG form A
Figure 2A:
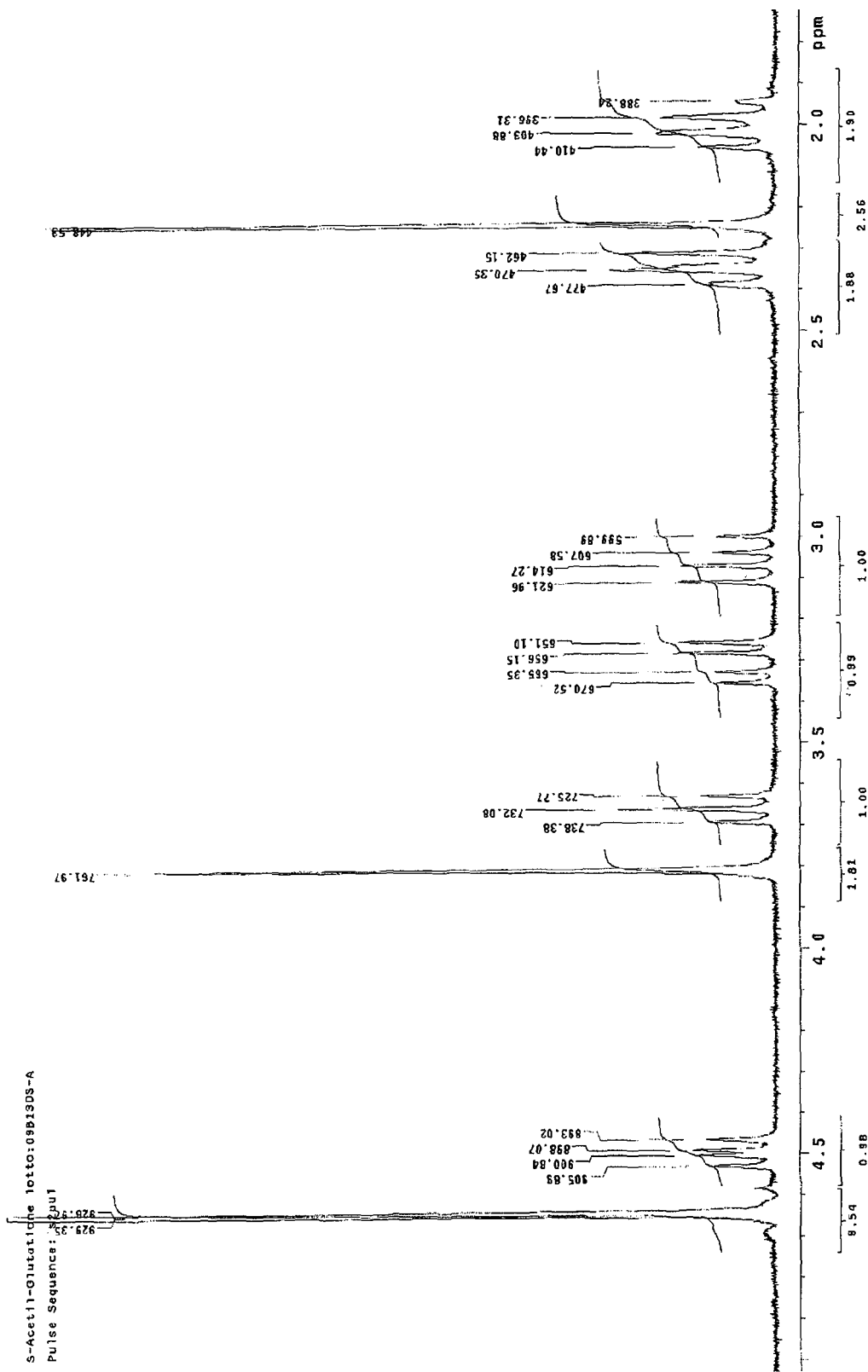
FIG. 2A: expansion of the 1H-NMR spectrum of SAG form A in the 1.8-5 ppm range
Figure 3:
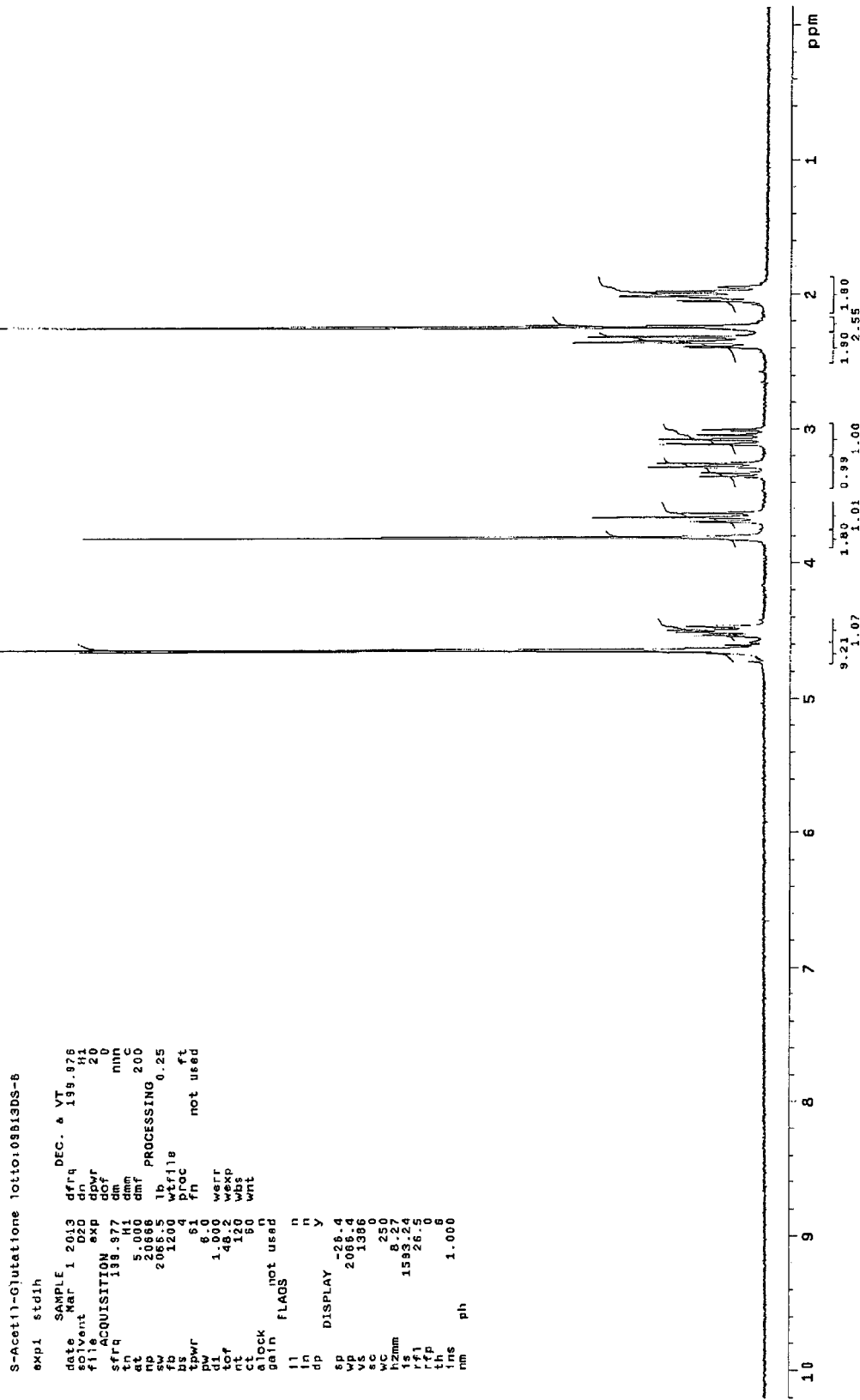
FIG. 3: 1H-NMR spectrum of SAG form B
Figure 3A:
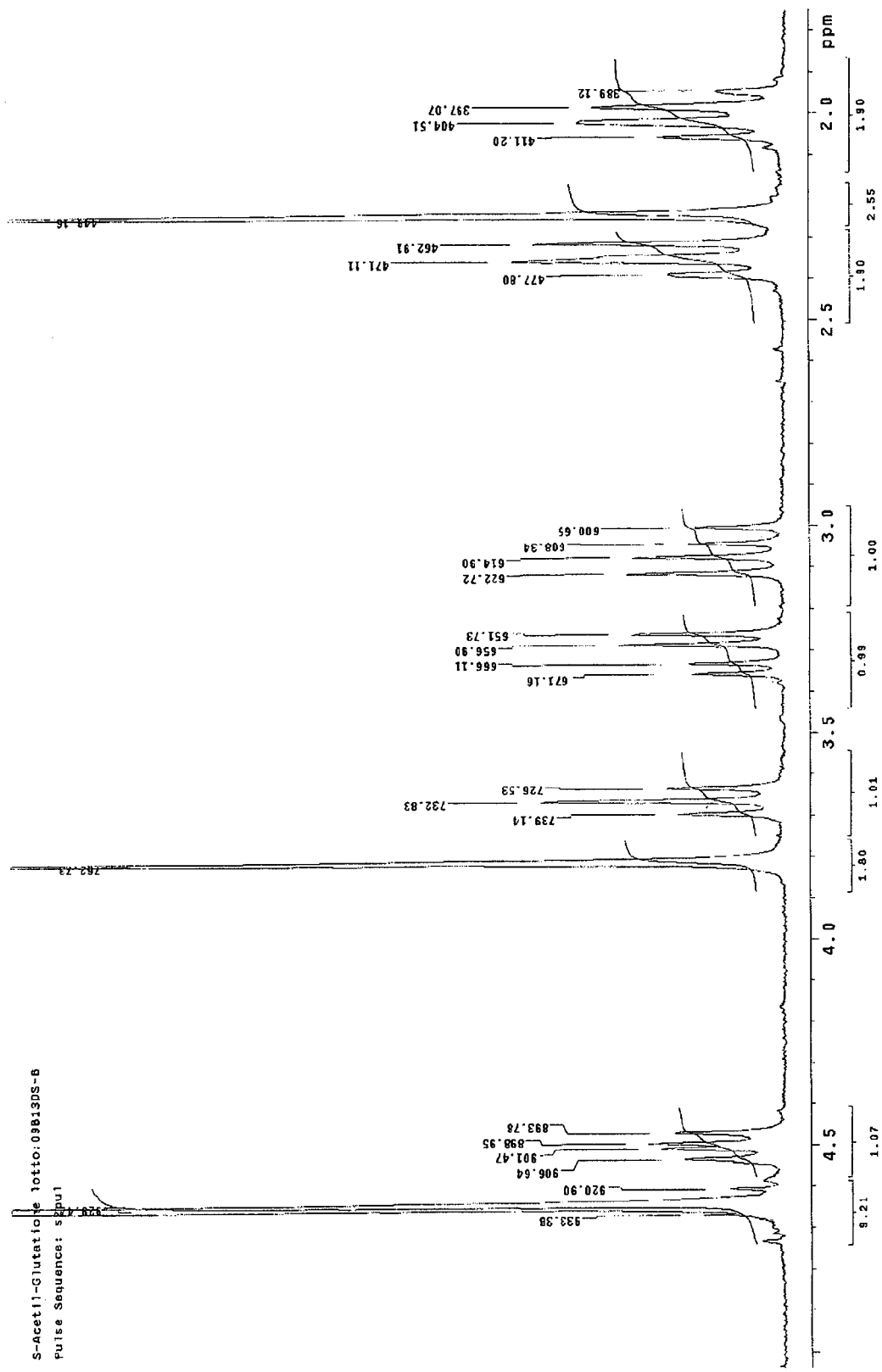
FIG. 3A: expansion of the 1H-NMR spectrum of SAG form B in the 1.8-5 ppm range

The product thus obtained presents the 1H-NMR spectra shown in FIG. 2 and FIG. 2A, the XRD diffractogram shown in FIG. 4, the FTIR spectrum shown in FIG. 6, the TGA pattern shown in FIG. 8, and the DSC thermogram shown in FIG. 10. The best-resolved diffraction peaks, and their relative intensities, are shown in Table 1.

Example 2

Preparation of SAG in Crystalline Form B 35 mL of demineralised water is heated to 75° C. When said temperature is reached, 5 g of crude SAG is added in a single addition with a hopper, and the reaction mass is returned to the temperature of 75° C., without exceeding the maximum temperature of 80° C. When the product has dissolved, which is checked by taking a sample under stirring, the solution is immediately cooled to 55° C., and 40 mL of acetone is added at the same temperature in about 10 min. The temperature is left to fall spontaneously to 20-25° C. under minimal stirring (60-120 rpm). The mixture is left under stirring at the same temperature for 2-12 h. It is then cooled to 5° C. and left under stirring at the same temperature for about 1 h.

The reaction mass is filtered, and washed with anhydrous acetone (2×10 mL) After drying for 14-18 h at 50° C. and 5 mbar of residual vacuum, 3.8 g of white crystalline solid corresponding to crystalline form B is obtained (yield 76%).

The analytical profile of the product thus obtained is:
Assay value: 99.3% (as is)
Impurities: Total: 0.8%; Single known impurities: GSH (0.2%), GSSG (1.1%)
Water 1.2%
Residual acetone: <0.1%
Apparent density: 0.25-0.40 g/mL The product thus obtained presents the 1H-NMR spectra shown in FIG. 3 and FIG. 3A, the XRD diffractogram shown in FIG. 5, the FTIR spectrum shown in FIG. 7, the TGA pattern shown in FIG. 9 and the DSC thermograms shown in FIGS. 11 and 12. The best-resolved diffraction peaks, and their relative intensities, are shown in Table 2.

Example 3

Preparation of SAG in Crystalline Forms A and B 35 mL of demineralised water is heated to 75° C., and 5 g of crude SAG is then added in a single addition with a hopper. The reaction mass is heated to 75° C., without exceeding the temperature limit of 80° C. When the product has dissolved, which is checked by taking a sample under stirring, the solution is cooled to a temperature ranging between 35° C. and 45° C. 40 mL of acetone is added to the solution at said temperature in about 10 min, under minimal stirring (60-120 rpm). The temperature is left to fall spontaneously to 20-25° C. At the end of the addition, the solution will be cloudy. The solution is maintained under stirring at the same temperature for 2-12 h, after which it is cooled to 5° C. and left under stirring for about 1 h. The reaction mass is filtered, and washed with anhydrous acetone (2×10 mL) After drying for 14-18 h at 50° C. and 5 mbar of residual vacuum, 4.0 g of white crystalline solid is obtained, corresponding to isomorphic crystalline forms A and B.

Apparent density: 0.35 g/mL.

The invention claimed is:

1. A crystalline form, designated form A, of S-acetyl-glutathione (SAG), characterised by an X-ray powder diffraction spectrum, obtained using the $\alpha_1$ and $\alpha_2$ radiations of copper at 1.54060 Å and 1.54439 Å respectively, having characteristic peaks, expressed in degrees 2-theta [°], at 5.2, 10.3, 15.4, 18.6, 19.7, 35.3, and 36.3±0.2.

2. The crystalline form of SAG according to claim 1, further characterised by an X-ray powder diffraction spectrum also having characteristic peaks, expressed in degrees 2-theta [°], at 20.4, 21.1, 25.1, 25.7, 27.0, 27.6, 27.9, and 32.7±0.2.

3. The crystalline form A of SAG according to claim 1, characterised by an IR spectrum, obtained in a potassium bromide matrix, with characteristic absorption bands at 3344, 1726, 1687 and 1663 $cm^{-1}$.

4. The crystalline form A of SAG according to claim 1, characterised by a DSC diagram having an endothermic decomposition peak between 190° C. and 210° C., obtained with a heating rate of 10.00° C./min.

5. The crystalline form A of SAG according to claim 4, characterised by a DSC diagram having an endothermic decomposition peak at 208.2° C.

6. A process to obtain the crystalline form A of SAG according to claim 1, comprising the following steps:
 a) dissolution of SAG in water at a temperature ranging from 75° C. to 80° C.;
 b) immediate cooling of the solution obtained in step a) to a temperature lower than 55° C., followed by further cooling until incipient crystallisation occurs;
 c) cooling to 20-25° C. of the mass obtained in step b) in the presence of stirring at the rate of 60-120 rpm, followed by further stirring of the mass at 20-25° C. for a time ranging from 2 to 12 hours;
 d) slow addition to the suspension obtained in c) of a solvent selected from the group consisting of acetone, ethanol and methanol, followed by cooling of the resulting suspension at a temperature ranging from 3° C. to 7° C.;
 e) recovery of the solid precipitated in step d), to give the crystalline form A of SAG.

7. A nutraceutical or pharmaceutical composition containing the crystalline form A of SAG according to claim 1, and a nutraceutically or pharmaceutically acceptable excipient.

8. A nutraceutical or pharmaceutical composition containing the crystalline form A of SAG according to claim 2, and a nutraceutically or pharmaceutically acceptable excipient.

9. A nutraceutical or pharmaceutical composition containing the crystalline form A of SAG according to claim 3, and a nutraceutically or pharmaceutically acceptable excipient.

10. A nutraceutical or pharmaceutical composition containing the crystalline form A of SAG according to claim 4, and a nutraceutically or pharmaceutically acceptable excipient.

* * * * *